United States Patent [19]
White et al.

[11] Patent Number: 6,106,686
[45] Date of Patent: Aug. 22, 2000

[54] ANCHOR FOR ELECTROPHORESIS GEL

[76] Inventors: Hugh W. White, 122 Washington St., Camden, Me. 04843; Douglas H. Robinson, 140 Talbot Ave., Rockland, Me. 04841; Richard B. Provonchee, Bird Point Rd., Cushing, Me. 04563

[21] Appl. No.: 09/178,219

[22] Filed: Oct. 23, 1998

[51] Int. Cl.[7] .......................... G01N 23/26; G01N 27/447

[52] U.S. Cl. .......................... 204/616; 204/456; 204/466; 204/606

[58] Field of Search .................................... 204/606, 607, 204/608, 610, 612, 615, 616, 617, 618, 621, 456, 457, 465, 466

[56] References Cited

U.S. PATENT DOCUMENTS 5,259,943  11/1993  Kezulic et al. .......................... 204/616
5,443,704   8/1995  Kirkpatrick et al. .................... 284/620

*Primary Examiner*—Jill Warden
*Assistant Examiner*—John S. Starsiak, Jr.
*Attorney, Agent, or Firm*—Seidel, Gonda, Lavorgna & Monaco, P.C.

[57] ABSTRACT

An anchoring device to be placed atop a slab of electrophoresis gel in a submerged electrophoresis process chamber includes a planar frame member shaped and sized to distribute weight evenly across the gel slab, particularly having a width dimension generally the same as the slab, and a plurality of legs spaced evenly around the frame. The legs have a length sufficient to raise the frame above the level of buffer liquid in process chamber, and have a blunt bottom surface in contact with the gel slab. The weight of the device and the even distribution of that weight is sufficient to anchor the gel slab and keep it submerged in the buffer liquid in the electrophoresis process chamber while making minimal contact with the slab and not distorting the electrical field through the gel, and without penetrating or lacerating the slab. The frame encloses one or more open window areas above the sample wells in the gel slab to permit easy access to load biological samples.

15 Claims, 3 Drawing Sheets

ANCHOR FOR ELECTROPHORESIS GEL

FIELD OF THE INVENTION

The present invention relates to the general field of the electrophoresis process and the gels used therein, and to the specific field of holders or anchors to retain the gel in place during the electrophoresis process.

BACKGROUND OF THE INVENTION

Gel electrophoresis is a process that has long been in use for clinical diagnosis and laboratory research. It is based upon the principle that electrically charged biological macromolecules will migrate through a solvent medium when subjected to an electrical field. Since macromolecules may vary in molecular weight and charge, it is possible to use an electrophoresis process to distinguish between different macromolecules based on their respective rates of movement through the solvent. Electrophoresis can also be used for other types of macromolecule analyzation, such as detecting amino acid changes.

In gel electrophoresis, the solvent is cast as a gel and solidifies into a thin planar slab. Originally, the laboratories mixed the gel and cast their own gel slabs on-site, and would inject the biological macromolecules samples into the slab. It soon became apparent, however, particularly as electrophoresis testing of DNA increased, that it is more convenient and more precise to use precast gel slabs made to uniform composition, size and configuration standards. The most common precast gel slab has a thin planar rectangular shape and includes a series of spaced wells along one or more side walls to receive the biological samples being investigated. Such gel slabs are inherently flimsy and subject to tearing and deformation if not handled gently. A particularly sensitive area is the thin walls separating the sample wells. While any deformation or tearing of the gel slab creates some risk of producing inaccurate tests, a breach between wells allowing commingling of adjacent biological samples would defeat the test purpose. Since the main risk of rough handling occurs during shipping, and the properties of the gel make visual detection of hairline cracks very difficult, it has been found important to protect the gels during shipping.

U.S. Pat. No. 5,443,704 discloses a packaging system for protecting the gel by packaging the gel in a plastic tub, with a foil-lined cover adhered to the top of the tub. In addition to protecting the gel during shipping, the tub can be placed directly into a submarine gel chamber and anchored in place by adhesive strips.

Where precast gel slabs are provided in packaging that cannot be placed in the gel chamber, however, some other means of anchoring the gel slab in a submerged position is required, since the gel nearly the same density as the buffer liquid and will float if it is not anchored. A means that has previously been used to anchor the gel involves a backing sheet adhesively attached to one flat side of the slab. The sheet extends beyond the edges of the slab to form a narrow overhang of sheet along the sides of the slab. A plastic anchor having two long thin beams, connected at the ends and having a thin bridge in the middle, is placed over the slab such that the long beams rest on the sheet overhang. The device is sold under a brand name "Catamaran", possibly because of its appearance. The Catamaran type anchor, however, anchors the backing sheet rather than the gel directly, so that if the gel slab becomes dislodged from the backing sheet when power is switched to the electrodes, the slab will float in the buffer liquid and cause a loss of sample from the wells or skewed electrophoretic patterns. In addition, the plastic backing sheet adhered to the gel precludes transfer of DNA to a solid support such as a nylon membrane, and can make DNA recovery more difficult.

Other than the Catamaran anchor described above, the object frequently used to anchor the bare slab is usually some handy laboratory device selected ad hoc, such as a glass rod or glass plate, and placed across a portion of the slab. While this is a practical solution, it is clearly not optimum, since the laboratory devices often cause distortions in the migration of macromolecules through the gel by interfering with the electrical field.

Consequently, it is an object of this invention to provide a device specifically designed to anchor a precast gel slab in a submarine gel chamber such that the slab does not float on the buffer fluid or become dislodged when electric current is passed between the electrodes. Specific design objectives are that the device anchor the slab by weight alone, rather than by some sort of adhesive or mechanical attachment, so that the anchor can be simply set on top of the gel slab.

Within that overall objective, however, is the consideration that the anchor not cause interference with the electrophoresis process. Consequently, related objectives are that the device have minimal contact with the gel slab, that its weight be evenly distributed over the slab, that the local pressure at the contact points not cause the contact points to lacerate or pierce the slab, and that the anchor provide easy access to the sample wells after it is in place atop the slab. The manner in which these objectives are achieved is described below.

SUMMARY OF THE INVENTION

The invention is a device to be placed atop a slab of electrophoresis gel in a submerged electrophoresis process chamber to anchor the slab. This anchoring device includes a planar frame member shaped and sized to distribute weight evenly across the gel slab, particularly having a width dimension generally the same as the slab, and a plurality of supports spaced evenly around the frame. The supports have a length sufficient to raise the frame above the level of buffer liquid in the electrophoresis chamber, and preferably have a blunt bottom surface in contact with the gel slab. The weight of the device and the even distribution of that weight is sufficient to anchor the gel slab and keep it submerged in the buffer liquid in the electrophoresis process chamber while making minimal contact with the slab and without penetrating or lacerating the slab. The frame encloses one or more open window areas above the sample wells in the gel slab to permit easy access to load biological samples.

DETAILED DESCRIPTION OF THE EMBODIMENTS

Figure 1:
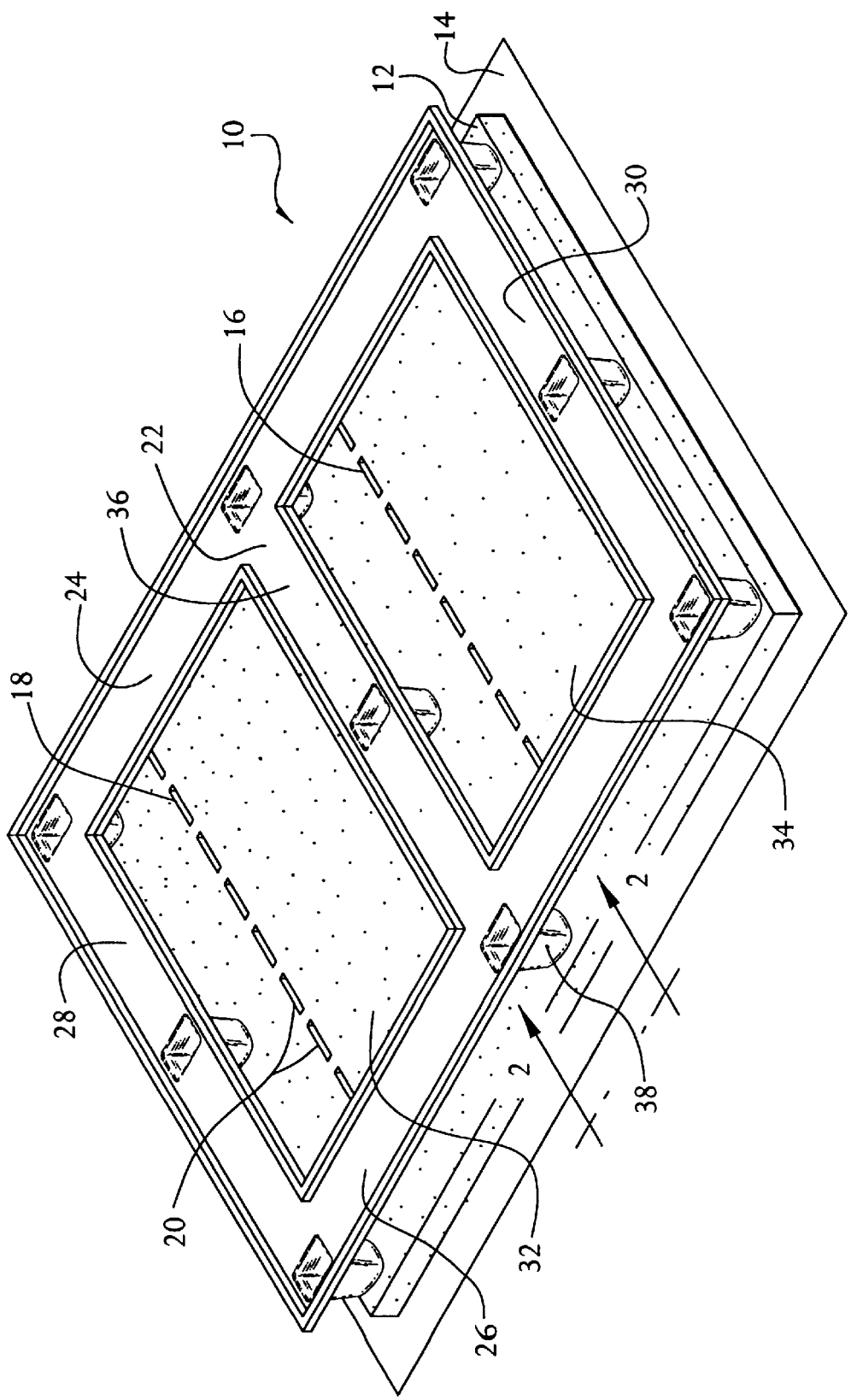
FIG. 1 is an isometric view of an electrophoresis gel anchor according to the present invention set upon a precast gel slab.

In FIG. 1, an anchoring device (10), or anchor is shown placed atop a slab of electrophoresis gel (12) on the platform

(14) of a submerged electrophoresis chamber. Details of the chamber are not important to the description of this invention and are therefore omitted from the drawings. The gel slab (12) described herein is an agarose gel precast into a 10×15 cm rectangular slab with two transverse rows (16, 18) of wells (20) that extend nearly through the slab and which are used to contain biological samples to be investigated. Gel slabs of this type are well known and come in a variety of sizes and well configurations. The particular type of gel is not, however, important to the invention, except to the extent that the size, shape and open areas configuration of the anchoring device will be selected according to the size, shape and well configuration of the gel slab.

The anchor (10) is preferably an integrally formed thermoplastic object, but for purpose of description it is helpful to describe it in parts. One part is a planer rectangular frame member (22). Since gel slabs come in varying sizes, the size of the frame (22) may be selected for use with a particular size slab. To achieve good weight distribution, the frame member should preferably have a width dimension generally corresponding to the width dimension of the gel slab it is designed to anchor, and even better weight distribution can be achieved if the frame member is shaped and sized to generally correspond with the circumference of the slab. For example, in the depicted embodiment, the frame member (20) is shaped and sized generally to the circumference of the gel slab (12), that is, the frame member (20) has a 10×15 cm rectangular circumference corresponding to the circumference of the gel slab. The frame could however, have shorter length, such as a 6×10 cm frame, and only one open window to provide access to the most interior well row (16). The more perimeter well row (18) would lie just outside the length of the frame. It should also be apparent that two or more anchoring devices could be could be used to anchor a lager slap with multiple rows of sample wells, such as two 10×15 cm anchors for a 20×25 cm slab.

Although it is a continuous piece of plastic material, the frame's planer rectangular shape can be described as being defined by two equal-length longitudinal side beams (24, 26) and two equal-length end (28, 30) beams. The frame member defines at least one, and in the depicted embodiment two, open areas (32, 34) above the sample wells (20) when the frame is placed atop the slab (12). In the depicted embodiment, the frame has a cross beam (36) connecting to the longitudinal side beams (24, 26) and located midway between the end beams (28, 30), which defines the open areas as two windows (32, 34) that are completely enclosed by the frame member, and are of sufficient size to permit easy access to the wells (20) to load biological samples therein. The open areas, however, need not be completely enclosed by the frame.

Figure 2:
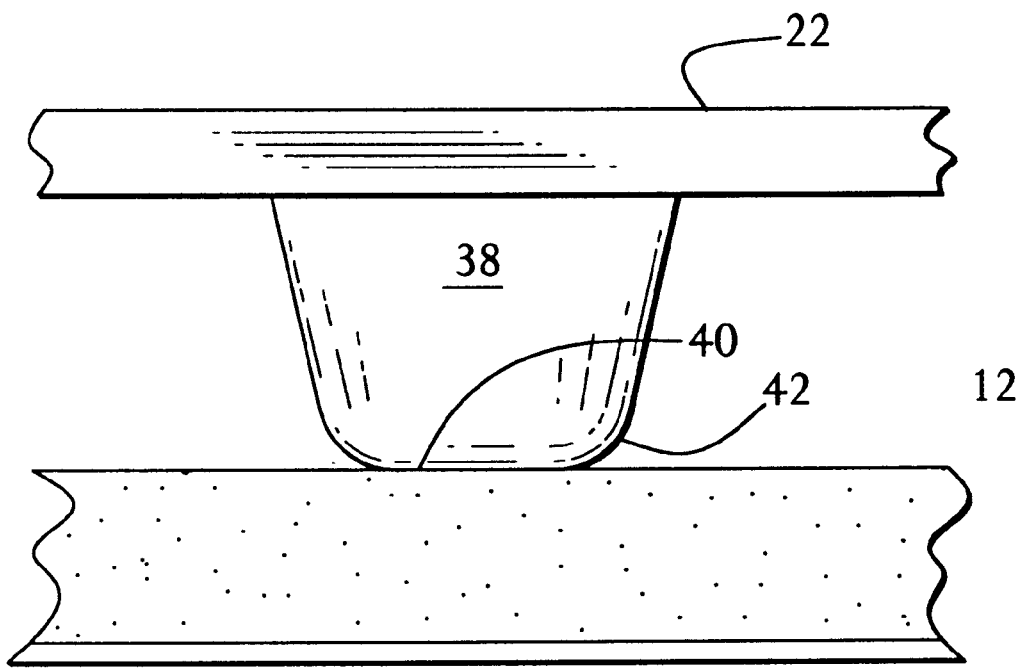
FIG. 2 is a side view of a limited section of the anchor and gel of FIG. 1, as viewed between and in the direction of the arrows 2—2 of FIG. 1.

To raise the frame member above the level of buffer liquid in the submerged electrophoresis process chamber when the anchoring device is placed on top of the gel slab, the anchor (10) has a plurality of supports, herein legs (38), depending from the frame member. The length of the supporting legs (38) should be selected to raise the bottom of the frame slightly (1–2 cm) above the surface of the buffer liquid. The weight of the anchoring device is chosen to be sufficient to anchor the slab against the platform (14) and the distribution of that weight over the gel slab is important to keep the flexible slab from bending upwards at the sides or in the center from the buoyant pressure or electroendosmosis. Thus, in the depicted anchor, there are nine supporting legs (38) spaced around the frame member in a generally regular spacing pattern to distribute the weight of the anchor at the sides and center of the slab. The legs provide minimal contact with the gel slab and do not penetrate or lacerate the surface of the slab, and so will not distort the electrophoresis process. Consequently, it is preferable that each leg have a blunt bottom surface, such as the flat surface (40) with rounded edges (42), as shown in FIG. 2, for contact with the gel slab. Other shapes of bottom surfaces could be provided for the legs, but should be blunt, rather than sharp edged or pointed, to prevent penetration or laceration of the gel.

Figure 4:
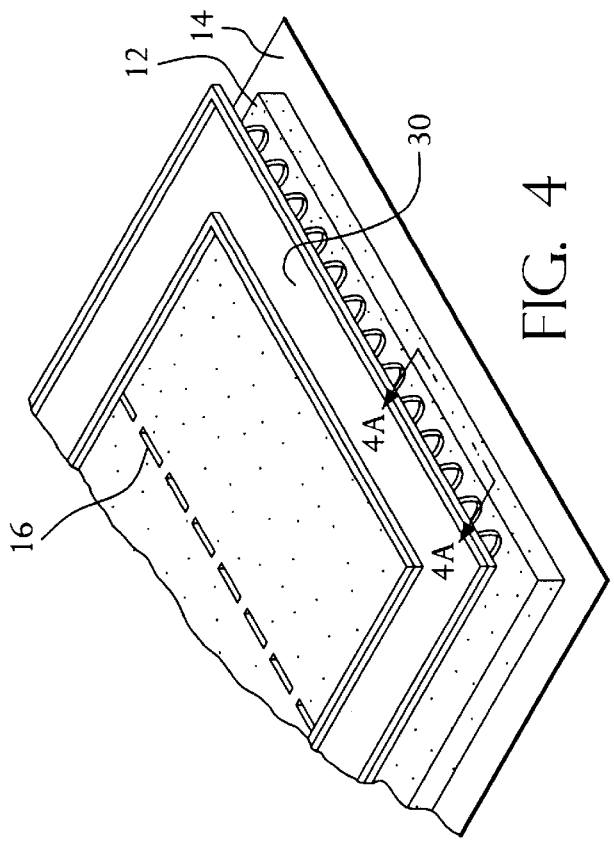
FIG. 4 is a partial isometric view of yet another embodiment of the gel anchor according to the present invention with spiral-type supporting members.
Figure 4A:
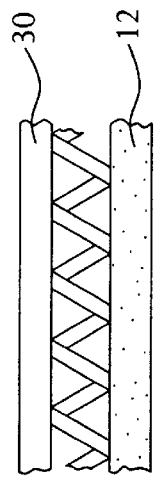
FIG. 4A is a partial side view of the spiral-type supporting members taken along lines 4A—4A in FIG. 4.

For economy and ease of construction, it is preferred that the anchor be an integral piece of formed high-density thermoplastic, such as, but not limited to clear glyocl-polyethylene terephthalate copolymer (PETG). It is also preferable that the legs be formed as hollow structures. Although the supports shown in this embodiment are legs, however, it may be acceptable to support the frame on top of the gel with other supporting members. For example, thin plastic bands wound in spiral and attached to the underside of the frame (see FIGS. 4 and 4A) would produce some cushioning effect when the frame is placed on the gel, as the spirals would flex under the weight of the frame. While fabrication of such spiral supports would be more complex than the forming of simple hollow legs, a frame with spiral supports should have equivalent capacity to anchor the gel without interfering in the electrophoresis process.

Figure 3:
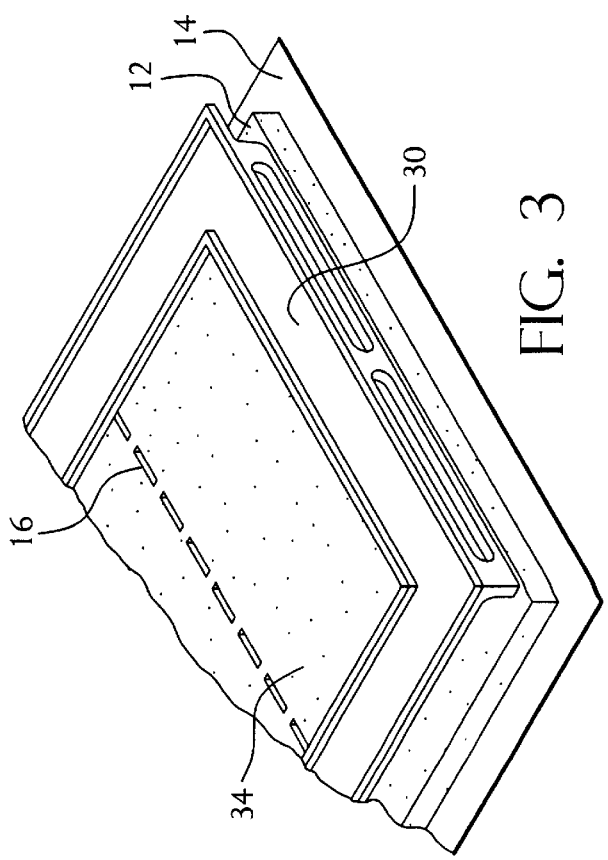
FIG. 3 is partial isometric view of an alternate embodiment of the gel anchor according to the present invention with open rails as the supporting members.

The supporting members should not, however, create a barrier across the surface of the gel slab which makes a significant interruption of the buffer liquid. The electrical potential between the electrodes causes electrical current to flow through the gel and through the buffer. If solid rails of non-conducting material such as plastic or glass were tried as supporting members across the gel slab, the current in the buffer would be interrupted and channeled into the gel, causing a distortion in the gel current. Thus, solid rails or other structure that create a significant interruption in the buffer liquid across the slab should not be used as supporting structure. An "open" rail, however, with large openings to allow an essentially contiguous buffer liquid on both sides of the rail, could be used as a supporting member (see FIG. 3).

Another consideration in the design of the legs or other supporting members is that they should not entrap pools of buffer liquid on the gel. The electrical current flow in the buffer produces heat. Convective movement of the liquid buffer in the chamber tends to transfer the heat away from the gel and to equalize the temperature throughout the buffer. Some electrophoresis chambers even provide cycling and cooling of the buffer. If the gel anchor trapped buffer in pools that inhibit convective movement, the temperature of the liquid trapped on the gel could rise enough to distort the macromolecule migration through the gel. Thus, legs as described above, and the alternative supporting members as described above, allow free convective movement of the buffer.

What is claimed is:

1. An anchoring device to be placed atop a slab of electrophoresis gel having a row of sample wells when the gel is used in a submerged electrophoresis process chamber, the anchoring device comprising:

a frame member; and a plurality of supporting members depending from the frame member and spaced around the frame member in a generally regular spacing pattern, the supporting members having a length sufficient to raise the frame member above the level of buffer liquid in the submerged electrophoresis process chamber when the anchoring device is placed on top of the gel slab, each supporting member further having a blunt bottom surface for contact with the gel slab;

wherein the weight of the device and the distribution of that weight over the gel slab is sufficient to anchor the gel slab in the chamber during the submerged electrophoresis process chamber without penetrating or lacerating the slab, and the frame member defines one or more open areas above the sample wells when the frame is placed atop the slab, the open areas being of sufficient size to permit easy access to the wells to load biological samples therein.

2. An anchoring device as in claim 1, wherein the frame has a width dimension generally corresponding to the width dimension of the gel slab it is intend to anchor.

3. An anchoring device as in claim 1, wherein the frame member is shaped and sized generally to the circumference of the gel slab it is intended to anchor.

4. An anchoring device as in claim 2, wherein the frame member is generally planar.

5. An anchoring device as in claim 3, wherein the frame member is generally planar.

6. An anchoring device as in claim 1 wherein there are two open areas.

7. An anchoring device as in claim 6, wherein the open areas are windows completely enclosed by the frame member.

8. An anchoring device as in claim 7, wherein the frame member has a is planar rectangular shape and the open areas are two rectangular windows formed by the frame.

9. An anchoring device as in claim 8, wherein the planer rectangular shape is defined by two equal-length longitudinal side beams and two equal-length end beams, the longitudinal beams having a greater length than the end beams.

10. An anchoring device as in claim 8, wherein the device is integrally formed of a thermoplastic material.

11. An anchoring device as in claim 1, wherein the device is integrally formed of a thermoplastic material.

12. An anchoring device as in claim 1, wherein the supporting members are legs.

13. An anchoring device as in claim 11, wherein the supporting members are hollow legs.

14. An anchoring device as in claim 1 wherein the supporting members are open rails.

15. An anchoring device as in claim 1, wherein the supporting members are thin plastic bands wound in spiral and attached to the underside of the frame.

* * * * *